United States Patent [19]

Montreuil et al.

[11] Patent Number: 5,021,560

[45] Date of Patent: Jun. 4, 1991

[54] IMMUNOGENIC FRACTION ACTIVE AGAINST BILHARZIOSES, ITS PREPARATION, AND IMMUNIZING COMPOSITIONS CONTAINING IT

[76] Inventors: Jean Montreuil, Geneviéve Spik, André58 rue du Capitaine Jasmin Capron, Colette Dissous, Jean-Marie Grzych, all of France

[73] Assignee: Institut Pasteur, Institut Pasteur De Lille, Institut National De La Sante Et De La Recherche Medicale-Inserm

[21] Appl. No.: 72,656

[22] Filed: Jul. 7, 1987

[30] Foreign Application Priority Data

Jul. 7, 1986 [FR] France .................. 86 09842

[51] Int. Cl.$^5$ ............... A61K 37/02; A61K 39/00; A61K 39/395; C04K 15/14
[52] U.S. Cl. .................. 536/1.1; 424/85.8; 424/86; 424/87; 530/395; 435/7.22; 435/810; 435/975; 436/548; 514/8; 514/9; 514/21
[58] Field of Search ............. 530/395; 424/85.8, 86, 424/87; 436/548; 435/7, 810; 536/1.1; 514/8, 9, 21

[56] References Cited

U.S. PATENT DOCUMENTS 4,384,992  5/1983  Capron et al. .................. 435/68

OTHER PUBLICATIONS

Annales de L'Institut Pasteur, A. Capron et al., "Les Antigenes de Schistosoma Mansoni", Nov. 1965, vol. 109, pp. 798–810.

Nature, J. M. Grzych et al., "An Anti–Idiotype Vaccine Against Experimental Schistosomiasis", 4 Jul. 1985, vol. 316, pp. 74–76.

Chemical Abstracts, Brenowitz et al., "Immunochemical Relationships and Subunit Composition of Molluskan Hemocyanin", vol. 106, 1987, abstract 115428V.

Primary Examiner—Ronald W. Griffin
Attorney, Agent, or Firm—Oblon, Spivak, McClelland, Maier & Neustadt

[57] ABSTRACT

The present invention relates to an immunogenic fraction active against bilharzioses. This glycoprotein extracted from hemocyanin of a mollusc, is characterized in that its glucidic fraction represents 5 to 25% of the glycoprotein molecule and in that the molar composition of said glucidic fraction (calculated on the basis of 3 mannose residues) is substantially the following:

|  | Monosaccharidic residues |
|---|---|
| Mannose | 3 |
| Galactose | 3 to 4 |
| Fucose | 2 to 3 |
| Glucose | 2 ± 0.2 |
| Xylose | 0.5–1 |
| N-acetylglucosamine | 3–4 |
| N-acetylgalactosamine | 2 ± 0.3 |

Use: immunizing compositions against bilharzioses.

43 Claims, 2 Drawing Sheets

IMMUNOGENIC FRACTION ACTIVE AGAINST BILHARZIOSES, ITS PREPARATION, AND IMMUNIZING COMPOSITIONS CONTAINING IT

BACKGROUND OF THE INVENTION

French Patent Application Nr. 8606281 of Apr. 30, 1986 describes a glycoprotein extracted from hemocyanin of Megathura crenulata, denoted in short as "KLH" and its oligosaccharidic epitope. It is shown in this patent that said glycoprotein has the same antigenic properties as the 38 KD antigen isolated from the surface of Schistosoma mansoni schistosomula and that the 38 KD antigen of the schistosomulum and the hemocyanin of Megathura crenulata both contain the same oligosaccharide which is the oligosaccharidic epitope aforementioned, which is recognized by a protective monoclonal antibody as being the epitope responsible for the antigenic power of the schistosomulum 38 KD antigen and of KLH, the protective monoclonal antibody being obtained from the IPL Sm1 hybridoma identified in the said french patent Application.

It is an object of the present invention to determine the chemical structure of the glycoprotein and of its oligosaccharidic epitope identified in the abovementioned french patent application and to enable its synthesis to be carried out.

GENERAL DESCRIPTION OF THE INVENTION

According to the present invention there is provided a glycoprotein extracted from KLH (hemocyanin of Megathura crenulata) which is characterized in that its glucidic fraction represents 5 to 5.25% of the glycoprotein molecule and in that the molar composition of said glucidic fraction (calculated on the basis of 3 mannose residues) is substantially as follows:

|  | Monosaccharide residues |
| --- | --- |
| Mannose | 3 |
| Galactose | 3 to 4 |
| Fucose | 2 to 3 |
| Glucose | 2 ± 0.2 |
| Xylose | 0.5–1 |
| N-acetylglucosamine | 3–4 |
| N-acetylgalactosamine | 2 ± 0.3 |

The monosaccharides which constitute the glucidic fraction of the KLH have been identified and measured by gas chromatography associated with mass spectrometry, which has permitted to establish the absence of O-methylated monosaccharides in said glucidic fraction.

According to the present invention there is also provided the glycanic fraction isolated from the aforesaid glycoprotein, extracted from KLH by proteolysis by pronase and purification of the hydrolysis product by gel-filtration chromatography to collect the product of the major peak obtained, of which the composition in glucides (calculated on the basis of 3 mannose residues) is substantially as follows:

|  | Number/monosaccharidic residues |
| --- | --- |
| Mannose | 3 |
| Galactose | 4 |
| Fucose | 1.6 |
| Glucose | 4 |
| Xylose | 0.23 |
| N-acetylglucosamine | 3.3 |
| N-acetylgalactosamine | 2 |

According to the present invention there is also provided a synthetic glycan substantially identical with the glycan extracted from KLH and the glycan of the 38 KD antigen of S. mansoni, which is characterized in that it has at least one of the following primary structures:

Glycans of N-glycosylproteins

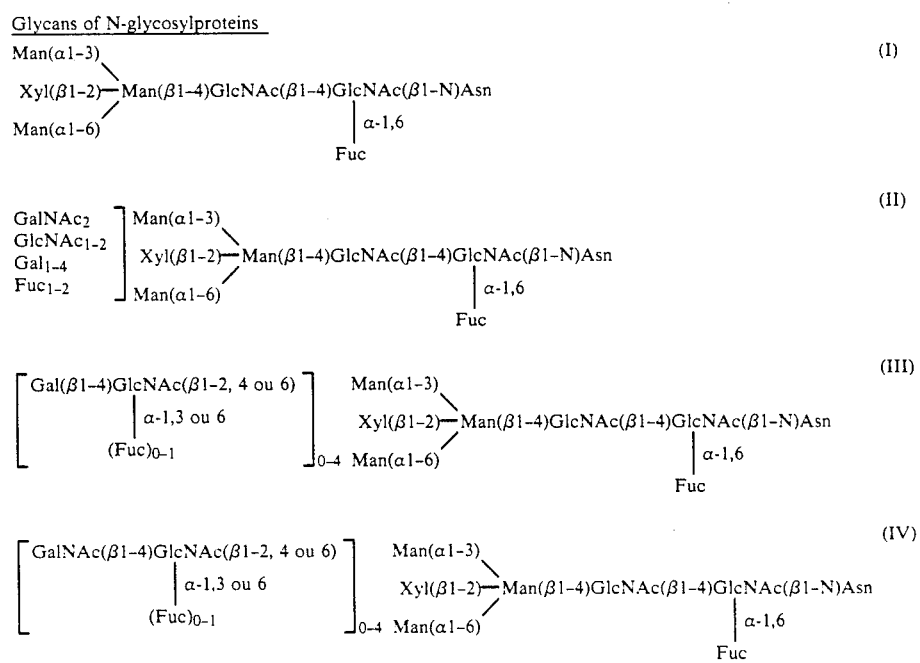

Glycans of O-glycosylproteins

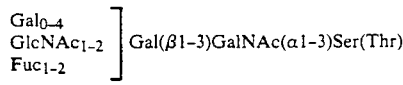

$$\left. \begin{array}{l} \text{Gal}_{0-4} \\ \text{GlcNAc}_{1-2} \\ \text{Fuc}_{1-2} \end{array} \right\} \text{Gal}(\beta 1\text{-}3)\text{GalNAc}(\alpha 1\text{-}3)\text{Ser}(\text{Thr}) \quad (V)$$

The antigenic activity of the glycans isolated from KLH or obtained by synthesis has been estimated by means of the specific monoclonal probe of the 38 KD molecule, namely the IPL Sml antibodies used in the above-mentioned French application by the technique of inhibition of the fixation of the IPL Sml antibody labelled with iodine 125, respectively on the glycoprotein extracted from KLH and on the synthetic glycan according to the present invention, by serums of animals immunized by KLH. The results obtained are presented in the accompanying FIG. 1 and show that the antibodies produced in the course of such an immunization induce inhibition levels identical with those observed respectively for the infection serums, for the "cold" IPL Sml antibody, for purified KLH or for the target antigen 38 KD.

This demonstration of the inhibiting activity of the glycan fraction identified according to the present invention, with respect to the monoclonal antibody directed against the 38 KD antigen of Schistosoma mansoni and against the glycoprotein extracted from the hemocyanin of Megathura crenulata, has confirmed definitively the preceding investigations which concluded that the epitope of the surface antigen 38 KD must be at least in part glycanic [FEBS LETTERS, DISSOUS et CAPRON, 162 (1983) p. 355-359 and MOLECULAR AND BIOCHEMICAL PARASITOLOGY, DISSOUS et Al., 16 (1985), p. 277-288].

Consequently according to the present invention there are also provided serums protective against infections by Schistosoma mansoni, immunogenic compositions, vaccines, immunizing agents and diagnostic reagents which are characterized in that their active constituent is the glycoprotein and/or the glycan identified in the foregoing. According to the present invention there is also provided a process for the preparation of the above-identified glycoprotein which consists in subjecting the hemocyanin of Megathura crenulata to at least one proteolysis treatment with pronase and isolating the product of the proteolysis by precipitation with a suitable precipitating agent, such as ethanol particularly.

According to a preferred embodiment of the process according to the present invention, the product of proteolysis isolated by precipitation, is subjected to a suitable purification treatment, preferably to a purification treatment by gel-filtration chromatography, after which the eluted fraction having the major peak is isolated by precipitation, to provide a purified glycopeptidic fraction.

As indicated above, the composition in glucides of the fractions so isolated has been determined qualitatively and quantitatively by gas chromatography coupled with mass spectrometry.

According to the invention, the O-glycosidically bonded glycans are released by the method of β-elimination in the form of oligosaccharide-alditols, the N-glycosidic bond is not affected.

The reaction is performed on 93 mg of pronasic glycopeptides.

The final solution resulting from the β-elimination is fractionated on a column of Biogel P2 equilibrated in water. The alkali-stable glycopeptides exceeding 1800 D, exclusion molecular weight of Biogel P2, are eluted at the dead volume of the column, whilst the O-glycans are delayed.

The locating of the eluted fractions is done by thin layer chromatography. In this way 4 fractions are isolated of which fraction A represents the major part (⅓) and corresponds to the alkali-stable glycopeptides. This fraction A is separated by passage over a column of Con A Sepharose 4B into 3 subfractions $A_1$, $A_2$, $A_3$, of which only the fraction $A_1$ preserves a biological activity comparable with that of the fraction A. This fraction $A_1$ isolated from the hemocyanin of Megathura crenulata is characterized by the following formula:

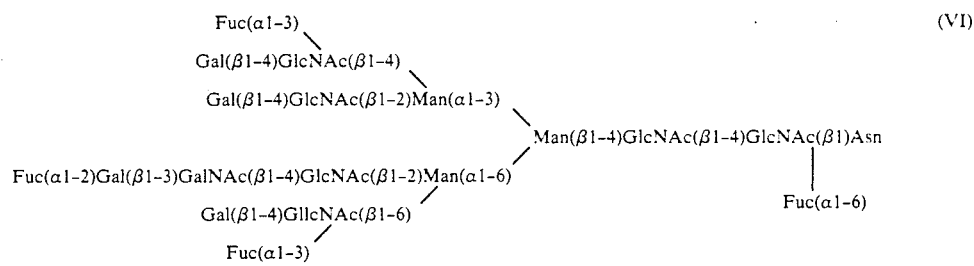

(VI)

The antigenic activity of the glycopeptidic fractions extracted from the hemocyanin of Megathura crenulata, identified above, and that of the synthetic glycans which correspond to one of the primary structures of formulae I to IV have been evaluated, among others, by means of the inhibition test mentioned above.

Beside the use mentioned above, the glycopeptides isolated from proteolysates of KLH, or the glycans released by chemical or enzymatic hydrolysis of KLH or again prepared by organic synthesis, according to the present invention, may be used for the preparation of neoglycoproteins, by condensation of said glycopeptides or glycans with natural or synthetic peptides.

In an advantageous embodiment of this process, the condensation of said glycopeptides or glycans with suitable peptides is performed by coupling of oligosaccharides and proteins.

According to another advantageous embodiment of this process, the preparation of the neoglycoproteins is effected by coupling glycopeptides and proteins.

As examples of peptides which can be condensed with the glycans according to the present invention, there can be cited tetanic anatoxin and/or synthetic peptides derived from protein 28 kDa.

The neoglycoproteins so-obtained have the advantage of grouping in a single chemical structure, two complementary antigenic activities, namely the antigenic activity of the glycan according to the present invention and the antigenic activity of the peptidic fraction associated with said glycan to form the desired neoglycoprotein.

Beside the foregoing features, the invention comprises still other features, which will emerge from the following description.

DESCRIPTION OF SPECIFIC EMBODIMENTS

Figure 1:
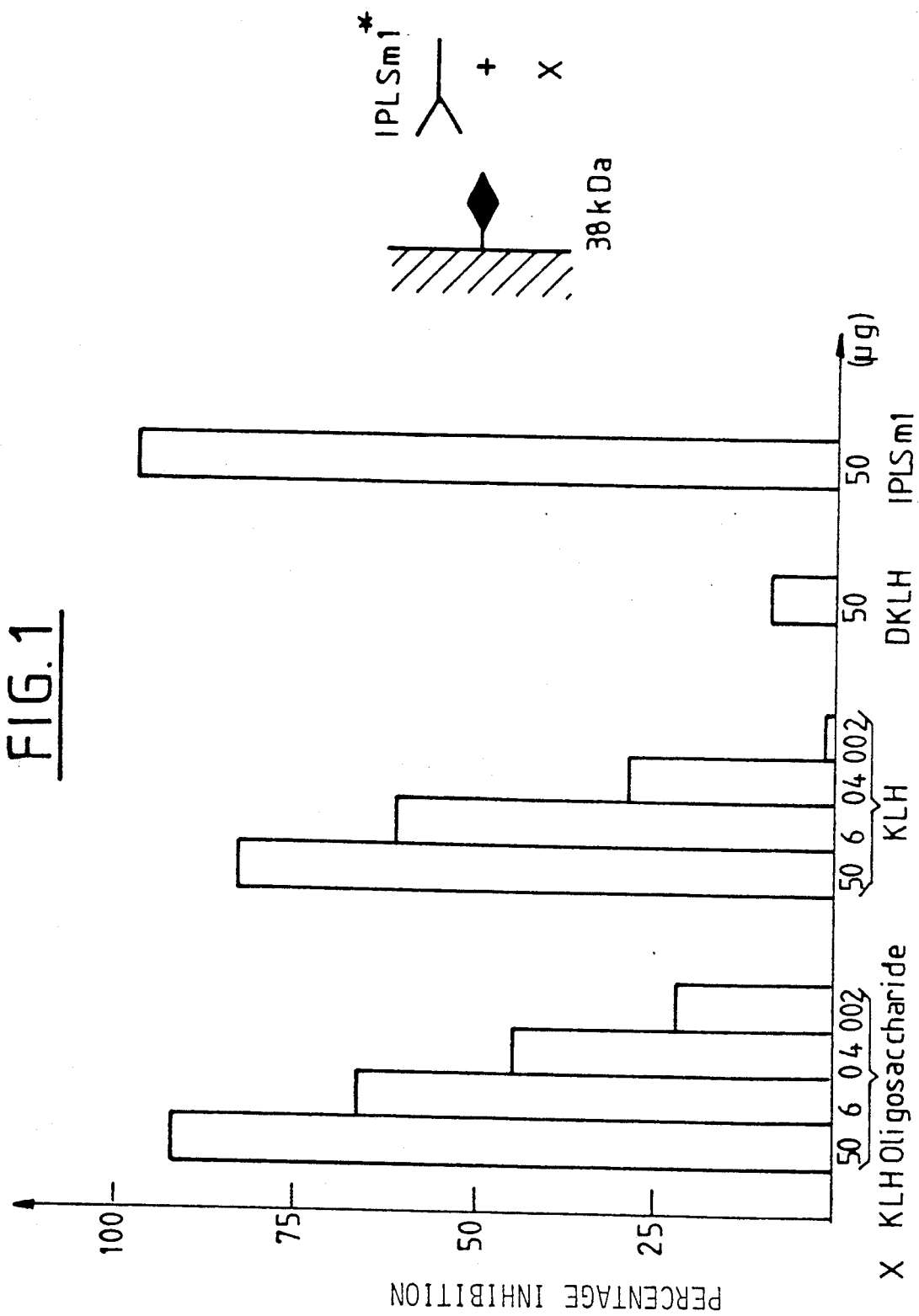

The invention will be better understood by means of the additional description which follows, which refers to examples of preparation of glycans according to the invention by extraction from KLH, of demonstration of the antigenic activity of said glycans and of preparation of neoglycoproteins also according to the present invention.

It must be well understood, however, that these examples are given purely by way of illustration of the invention, of which they do not constitute in any way a limitation thereof.

EXAMPLE 1

Preparation of glycopeptides according to the invention by extraction from KLH.

1. Hemocyanin of Megathura crenulata (KLH) is placed in contact with pronase in a ratio enzyme/substrate of the order of 1/50 to effect the proteolysis of the KLH; the reaction is carried out at a temperature of 40° C., at pH 8.2, for a period of 48 hours. The product of the proteolysis is isolated by precipitation with ethanol.

The proteolysis reaction followed by precipitation, is repeated twice.

2. The final product obtained at the end of the third proteolysis process is purified by gel-filtration chromatography on "Biogel" P-2.
3. The product eluted in the major peak contains the active glycan still bonded to a short peptidic chain.

Its glucide composition is checked by gas phase chromatography coupled with mass spectrometry.

Its antigenic activity is checked by the radio-immunological technique of inhibition of the fixation of the monoclonal antibody IPL Sml to the glycan, as described for KLH and the antigen 38 KD in the French patent application Nr. 86 06281 already mentioned.

EXAMPLE 2

Preparation of the glycans according to the invention by extraction from KLH or from KLH glycopeptides.

The N-glycosidically linked glycans are released by the process of Lee and Scocca (J. Biol. Chem., 247 1972) 5753-5758): a solution of KLH or of its glycopeptides in NaOH M - $KBH_4$ is kept at 100° C. for 6 h. The reaction is stopped by the addition, at 0° C., of formic acid until a pH of 4 is obtained. The glucidic fraction is purified by gel-filtration on Biogel P-2, the elution being performed with water. The N-reacetylation of the oligosaccharides in saturated solution of sodium bicarbonate is carried out with acetic anhydride whose action is continued for 2 h. The glucidic fraction is then purified by chromatography on Biogel P-2.

The O-glycosidically linked glycans are specifically released by elimination by β-elimination by treating the KLH or the glycopeptides derived therefrom by the preceding procedure with the exception of the conditions of sodic attack which is done in the presence of 0.1 M NaOH - 1 M $KBH_4$, at 45° C. for 24 h.

EXAMPLE 3

Characterization tests of the antigenic activity of the glycans according to the present invention.

1°: Technique of inhibition of the fixation of the IPLSml antibody to the 38 kDa antigen of S. mansoni by oligosaccharides extracted from KLH.

This radioimmunological technique in solid phase is based on the inhibition of the fixation of the IPLSml antibody labelled with Iodine 125 to its target antigen by different antibodies or antigenic preparations.

a) Preparation of the solid phase

Each polyvinyl plate alveole is treated with 100 μl of a 10 μg/ml solution of $C_3$-109 monoclonal antibody (anti-S. mansoni antibody of IgM isotype which does not cross-react with the epitope of IPLSml antibody). This methodology enables the subsequent fixation of the 38 KD antigen. After 2 h of contact at 20° C., the plates are washed 3 times with 200 μl of 10 mM phosphate Buffer containing 0.1% of bovine serum albumin (BSA), and saturated 30 minutes at 20° C. with 200 μl of a 2% solution of BSA in phosphate Buffer. The plates are then washed three times in a 10 mM phosphate buffer 0.1% BSA and treated with 100 μl of a membranal extract of schistosomulum obtained by the technique described by DISSOUS et Al. in Mol. Biochem. Parasitol. (1981), 3, pages 215-225 (100 μl of antigenic solution at 100 μg/ml for each alveole). After 2 h incubation at 37° C. and 3 washings with 200 μl of 10 mM phosphate Buffer 0.1% BSA, the plates are ready for the inhibition reaction.

b) Inhibition reaction 50 microliters of IPLSml antibody labelled with iodine 125 (100,000 cpm in 50 μl) and 50 μl of the different antigenic fractions (50 at 0.02 μg/alveole) of KLH oligosaccharide, native KLH or 50 μg of deglycosylated KLH controls (DKLH), cold IPLSml antibody are incubated 1 h at 37° C., then overnight at 4° C. The plates are then washed 3 times in 10 mM phosphate Buffer 0.1% of BSA, and the alveoles counted separately with the gamma counter.

c) Expression of the results

The percentage inhibition of fixation of the antibody IPLSml is evaluated with respect to a negative control in which the 50 μl of labelled IPLSml are incubated in the presence of 50 μl of 10 mM phosphate Buffer 0.1% of BSA and this is shown in the accompanying FIG. 1.

2°: Technique of inhibition of the fixation of IPLSml antibodies on the hemocyanin of Megathura crenulata by the oligosaccharides extracted from the hemocyanin of Megathura crenulata.

This radioimmunological technique in solid phase is directly inspired from the method of evaluation of the inhibition of the fixation of the IPLSml antibody to its target antigen 38 KD. In this particular case, the solid phase is constituted by polyvinyl plates previously treated with KLH.

a) Solid phase

Each polyvinyl plate alveole is treated with 100 μl of a solution of KLH at 10 μg/ml in a 10 mM phosphate buffer with 0.1% of BSA for 2 h at 20° C. The plates are then washed 3 times in a 10 mM phosphate buffer with 0.1% of BSA and saturated with a 2% solution of BSA in 10 mM phosphate buffer, 30 minutes at 20° C. (200 μl per alveole). The excess BSA is removed by 3 washings (200 ul per alveole) in 10 mM phosphate buffer with 0.1% of BSA.

b) Inhibition reaction

Figure 2:
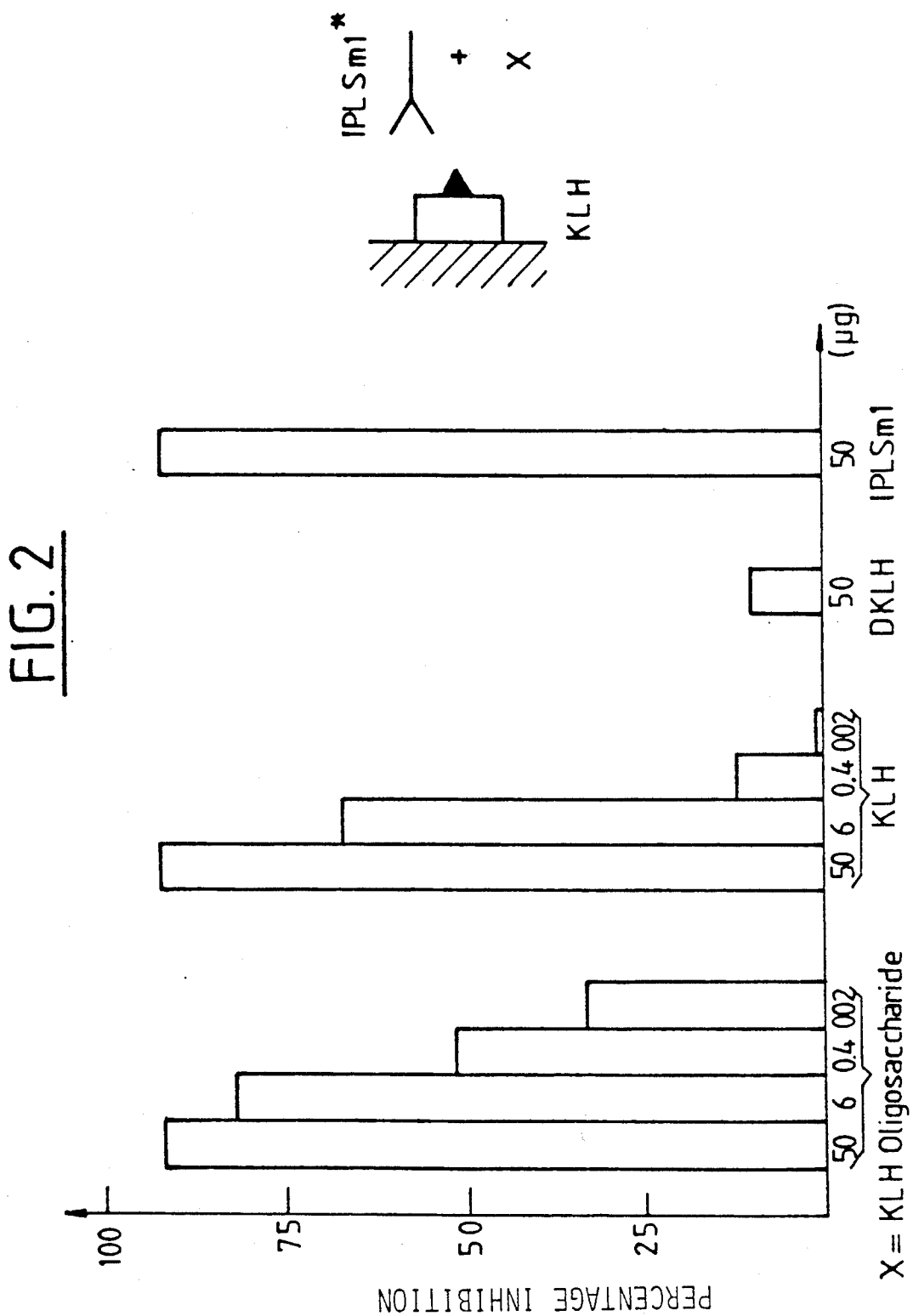

It is carried out under the same conditions as those defined in the case of the inhibition test of the fixation of the IPLSml antibody to its 38 KD antigen described in the 1° of the present Example, and its results are shown in accompanying FIG. 2.

ExAMPLE 4

Preparation of neoglycoproteins according to the present invention.

I - By coupling of oligosaccharides and proteins.

The oligosaccharide-protein coupling may be carried out according to the following experimental procedures, the protein used being either tetanic anatoxin, or synthetic peptide fragments of the 38 kD antigen.

1) Method of Gray (Gray G. R., Methods in Enzymology, 197, Colowick and Kaplan ed., Acad. Press, p. 155–162).

The principle of the method rests on the fact that sodium cyanoborohydride easily reduces the Schiff bases resulting from the condensation of an oligosaccharide with a primary amine, whilst being without effect on the carbonyl functions.

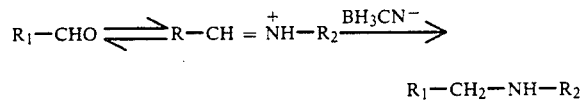

$$R_1-CHO \rightleftharpoons R-CH=\overset{+}{N}H-R_2 \xrightarrow{BH_3CN^-} R_1-CH_2-NH-R_2$$

The experimental protocol comprises the following steps: 0.5 μmol of protide, 150 μmol of oligosaccharide and 0.8 mmol of sodium cyanoborohydride are dissolved in 2.5 ml of potassium phosphate buffer 0.2 M (pH 8) and the solution is kept at 37° C. for 10 days.

The solution is then dialyzed against distilled water, then subjected to chromatography on Bio-gel P-6.

The number of oligosaccharidic residues coupled to the protein is then determined by colorimetric measurement. It is generally of the order of 15 to 20 glycans per protein molecule.

2) Method of Zopf et al. (Zopf, D. A., Tsai C-M and Ginsburg V., Methods in Enzymology, 1978, Colowick and Kaplan ed. Acad. Press, p. 163-169).

This method has the merit of being applicable to small amounts of substrate. The oligosaccharide is first of all coupled to the β-(p-aminophenyl) ethylamine, in the presence of sodium borohydride. The oligo-saccharide-phenethylamine is then coupled to the protide through a diazo-compound.

a) Preparation of the oligosaccharide-phenethyl amine 10 mg of oligosaccharide are added to 0.1 ml of β-(p-aminophenyl) ethylamine and the solution is stirred for 15 h in a sealed tube at ambiant temperature.

The alkylglycoside is obtained by addition of 0.2 ml of alcohol containing 3 mg of sodium borohydride, then isolated by chromotography on Bio-gel P-2.

b) Coupling of the oligosaccharide-phenethylamine derivative with a protide.

To a solution of 10 μmol of oligosaccharide-phenethylamine in 2 ml of water are added successively 0.8 ml of 0.1 N HCl and 0.6 ml of a solution of sodium nitrite at 2 mg/ml.

After 30 minutes of reaction, the mixture is slowly added to 6 ml of a protein solution (0.8 μmol) in 0.05 N NaOH. After 4 h reaction, the coupled product is dialyzed, then purified on Bio-gel P-6.

The sugar:protein ratio can reach 15 to 20.

II. By coupling of glycopeptides and proteins 100 mg of proteins are dissolved in 10 ml of borate buffer of pH 9.5. To the solution cooled to 0° C., are added 0.2 ml of toluene-2,4 diisocyanate (TDIC). The mixture is stirred 30 minutes at 0° C., left overnight at 4° C. and centrifuged to sediment the excess TDIC.

The supernatent is collected, stirred still 1 h at 0° C., centrifuged if necessary, then added to 10 ml of borate buffer pH 9.5 containing 10 to 20 micromoles of glycopeptides. The mixture is stirred 1 h at 37° C., dialyzed against 0.1 M ammonium carbonate (48 h), then against distilled water before being lyophilized.

The amount of glycopeptides conjugated to the protein is determined by colorimetric determination of the glucides.

This process is adapted from that of Schick A. F. and Singer S. J. (J. Biol. Chem. 236 (1961) 2477–2485).

We claim:

1. A glycoprotein extract obtained by proteolysis of the hemocyanin of a mollusc taken from the group comprising Megathura crenulata, wherein the glucidic fraction of said extract represents 5 to 5.25% of the glycoprotein and the molar composition of said glucidic fraction, calculated on the basis of 3 mannose residues, is substantially as follows:

|  | Monosaccharidic residues |
|---|---|
| Mannose | 3 |
| Galactose | 3 to 4 |
| Fucose | 2 to 3 |
| Glucose | 2 ± 0.2 |
| Xylose | 0.5–1 |
| N-acetylglucosamine | 3–4 |
| N-acetylgalactosamine | 2 ± 0.3. |

2. A glycopeptidic fraction isolated from the glycoprotein extract of claim 1 by a purification treatment of said glycoprotein extract by gel filtration chromatography, to obtain said glycopeptidic fraction having a composition in glucides, calculated on the basis of 3 mannose residues, substantially as follows:

|  | Nmbr/monosaccharidic residues |
|---|---|
| Mannose | 3 |
| Galactose | 4 |
| Fucose | 1.6 |
| Glucose | 4 |
| Xylose | 0.23 |
| N-acetylglucosamine | 3.3 |
| N-acetylgalactosamine | 2. |

3. A glycanic fraction obtained by alkaline treatment of hemocyanin of Megathura crenulata followed by N-reacetylation of the alkaline treated hemocyanin and purification of the reacylated hemocyanin on Biogel-P-2.

4. A synthetic glycan having one of the following structures I, II, III, IV or V:

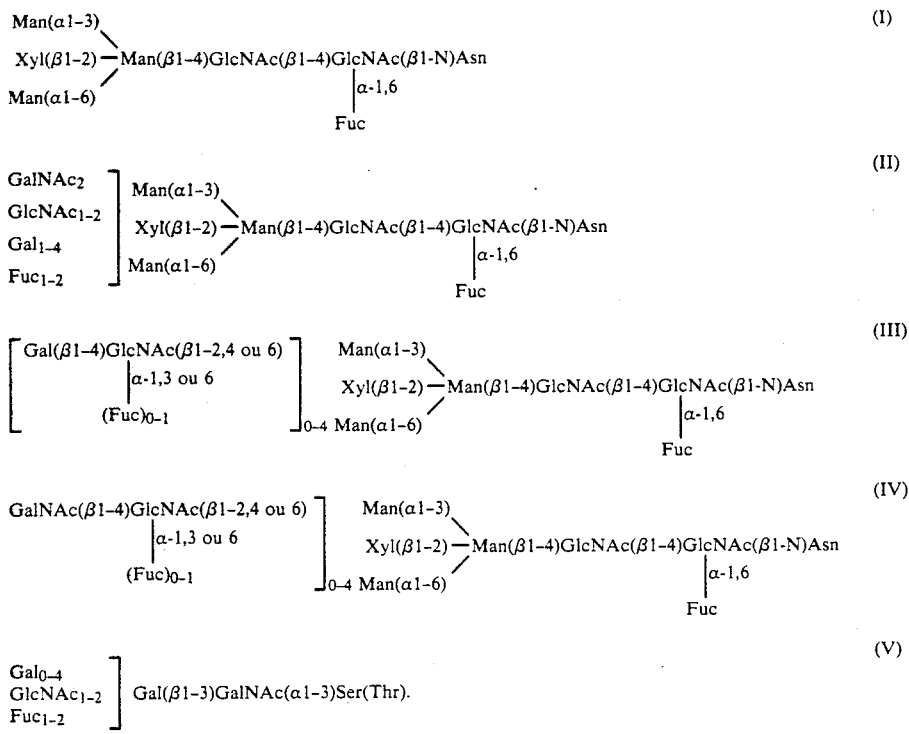

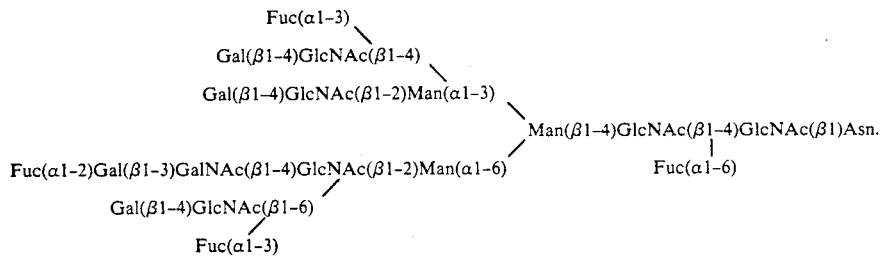

5. A glycan comprising fucose, galactose, xylose, mannose, N-acetylglucosamine, N-acetylgalactosamine and having the following structure (VI):

```
                Fuc(α1-3)
                        \
        Gal(β1-4)GlcNAc(β1-4)
                             \
        Gal(β1-4)GlcNAc(β1-2)Man(α1-3)
                                      \
                                       Man(β1-4)GlcNAc(β1-4)GlcNAc(β1)Asn.
                                      /                    |
Fuc(α1-2)Gal(β1-3)GalNAc(β1-4)GlcNAc(β1-2)Man(α1-6)       Fuc(α1-6)
                                      /
                    Gal(β1-4)GlcNAc(β1-6)
                                      /
                               Fuc(α1-3)
```
(VI)

6. A protective serum against infections by Schistosoma mansoni, comprising a serum of a mammal immunized by the glycoprotein extract of claim 1.

7. An immunogenic composition, comprising as an active constituent, a sufficient amount of the glycoprotein extract of claim 1 and a carrier or diluent.

8. A vaccine against bilharzioses, comprising an active vaccinating amount of the glycoprotein extract of claim 1 and a carrier or diluent.

9. An immunizing composition, comprising a complex formed by the coupling of an anti-idiotype antibody of a monoclonal anti-Schistosoma mansoni antibody to the glycoprotein extract of claim 1.

10. A diagnostic composition suitable for use in the seroepidemiology of bilharzioses, comprising an effective amount of the glycoprotein extract of claim 1 and a carrier or diluent.

11. A process for the preparation of the glycoprotein extract of claim 1, comprising subjecting the hemocyanin of Megathura crenulata to at least one proteolysis treatment with pronase and isolating the product of the proteolysis treatment by precipitation in ethanol.

12. The process of claim 11, further comprising purifying said glycoprotein extract by gel filtration chromatography and isolating the purified glycopeptidic fraction by precipitation.

13. A process for preparing the glycanic fraction of claim 3, comprising subjecting the hemocyanin of Megathura crenulata or glycopeptides thereof to alkaline hydrolysis followed by N-reacylation and purification by molecular sieve chromatography to obtain said glycanic fraction.

14. A process for preparing a neoglycoprotein, comprising condensing the glycopeptidic fraction of claim 2 with a natural or synthetic peptide having an antigenic activity complementary with the antigenic activity of said glycopeptidic fraction.

15. A process for preparing a neoglycoprotein, comprising condensing the glycanic fraction of claim 3 with a natural or synthetic having an antigenic activity complementary with the antigenic activity of said glycanic fraction.

16. A process for preparing a neoglycoprotein, comprising condensing the synthetic glycan of claim 4 with a natural or synthetic peptide having an antigenic activity complementary with the antigenic activity of said synthetic glycan.

17. The process of claim 14, 15 or 16, wherein said condensation is performed by coupling.

18. The process of claim 14, 15 or 16 wherein said peptide is selected from the group consisting of tetanic anatoxin, synthetic peptides derived from the protein 28 KD, and mixtures thereof.

19. A neoglycoprotein, obtained by the process of claim 14.

20. A glycanic fraction obtained by alkaline treatment of the glycoprotein extract of claim 1 followed by N-reacetylation of the alkaline treated extract and purification of the reacylated extract on Biogel-P-2.

21. A glycanic fraction obtained by alkaline treatment of the glycopeptidic fraction of claim 2 followed by N-reacetylation of the alkaline treated fraction and purification of the reacylated fraction of Biogel-P-2.

22. A protective serum against infections by Schistosoma mansoni, comprising a serum of a mammal immunized by the glycopeptidic fraction of claim 2.

23. A protective serum against infections by Schistosoma mansoni, comprising a serum of a mammal immunized by the glycan of claim 3.

24. A protective serum against infections by Schistosoma mansoni, comprising a serum of a mammal immunized by the glycan of claim 4.

25. A protective serum against infections by Schistosoma mansoni, comprising a serum of a mammal immunized by the glycan of claim 5.

26. An immunogenic composition, comprising as an active constituent, a sufficient amount of the glycopeptidic fraction of claim 2 and a carrier or diluent.

27. An immunogenic composition, comprising as an active constituent, a sufficient amount of the glycanic fraction of claim 3 and a carrier or diluent.

28. An immunogenic composition, comprising as an active constituent, a sufficient amount of the glycan of claim 4 and a carrier or diluent.

29. An immunogenic composition, comprising as an active constituent, a sufficient amount of the glycan of claim 5 and a carrier or diluent.

30. A vaccine against bilharzioses, comprising an active vaccinating amount of the glycopeptidic fraction of claim 2 and a carrier or diluent.

31. A vaccine against bilharzioses, comprising an active vaccinating amount of the glycanic fraction of claim 3 and a carrier or diluent.

32. A vaccine against bilharzioses, comprising an active vaccinating amount of the glycan of claim 4 and a carrier or diluent.

33. A vaccine against bilharzioses, comprising an active vaccinating amount of the glycan of claim 5 and a carrier or diluent.

34. An immunizing composition, comprising a complex formed by the coupling of an anti-idiotype antibody of a monoclonal anti-Schistosoma mansoni antibody to the glycopeptidic fraction of claim 2.

35. An immunizing composition, comprising a complex formed by the coupling of an anti-idiotype antibody of a monoclonal anti-Schistosoma mansoni antibody to the glycanic fraction of claim 3.

36. An immunizing composition, comprising a complex formed by the coupling of an anti-idiotype antibody of a monoclonal anti-Schistosoma mansoni antibody to the glycan of claim 4.

37. An immunizing composition, comprising a complex formed by the coupling of an anti-idiotype antibody of a monoclonal anti-Schistosoma mansoni antibody to the glycan of claim 5.

38. A diagnostic composition suitable for use in the seroepidemiology of bilharzioses, comprising an effective amount of the glycopeptidic fraction of claim 2 and a carrier or diluent.

39. A diagnostic composition suitable for use in the seroepidemiology of bilharzioses, comprising an effective amount of the glycanic fraction of claim 3 and a carrier or diluent.

40. A diagnostic composition suitable for use in the seroepidemiology of bilharzioses, comprising an effective amount of the glycan of claim 4 and a carrier or diluent.

41. A diagnostic composition suitable for use in the seroepidemiology of bilharzioses, comprising an effective amount of the glycan of claim 5 and a carrier or diluent.

42. A neoglycoprotein obtained by the process of claim 17.

43. A neoglycoprotein obtained by the process of claim 18.

* * * * *

UNITED STATES PATENT AND TRADEMARK OFFICE
CERTIFICATE OF CORRECTION

PATENT NO. : 5,021,560
DATED     : June 4, 1991
INVENTOR(S) : Jean Montreuil et al.

It is certified that error appears in the above-identified patent and that said Letters Patent is hereby corrected as shown below:

Title page: Item (76) inventors should read,

--Jean Montreuil, Villeneuve D'Ascq; Geneviève Spik, Marcq en Baroeul; André Capron, Phalempin; Colette Dissous, Sainghin en Melantois; Jean-Marie Grzych Marcq en Baroeul; all of France--.

Signed and Sealed this

Tenth Day of November, 1992

*Attest:*

DOUGLAS B. COMER

*Attesting Officer*    Acting Commissioner of Patents and Trademarks